United States Patent [19]

Sawa et al.

[11] Patent Number: 5,266,485
[45] Date of Patent: Nov. 30, 1993

[54] METHOD OF MANUFACTURING OPTICALLY ACTIVE (−)-2-HALO-1-(SUBSTITUTED PHENYL) ETHANOL BY KETONE REDUCTION

[75] Inventors: Ikuo Sawa; Yuko Konishi; Shunichi Maemoto, all of Takasago; Junzo Hasegawa, Akashi, all of Japan

[73] Assignee: Kanegafuchi Kagaku Kogyo Kabushiki Kaisha, Osaka, Japan

[21] Appl. No.: 829,018

[22] PCT Filed: Jul. 22, 1991

[86] PCT No.: PCT/JP91/00973

§ 371 Date: Mar. 6, 1992

§ 102(e) Date: Mar. 6, 1992

[87] PCT Pub. No.: WO92/01804

PCT Pub. Date: Feb. 6, 1992

[30] Foreign Application Priority Data

Jul. 24, 1990 [JP] Japan .................. 2-195808
Feb. 1, 1991 [JP] Japan .................. 3-033534

[51] Int. Cl.$^5$ .................. C12P 41/00; C12P 7/22
[52] U.S. Cl. .................. 435/280; 435/156; 435/911; 435/921; 435/924; 435/938; 435/942
[58] Field of Search .................. 435/280, 136, 156, 911, 435/921, 924, 938

[56] References Cited

U.S. PATENT DOCUMENTS

4,857,488  8/1989  Kutsuki et al. .................. 435/280

FOREIGN PATENT DOCUMENTS

21806  1/1981  European Pat. Off. .

OTHER PUBLICATIONS

Christen, M. et al., J. Chem. Soc., Chem. Commun. 1988: 264–266.
Hummel, W.; Appl. Microbiol. Biotechnol. 34:15–19 (1990).
Imuta, M.; J. Org. Chem. 45:3352–3355 (1980).
Jones, B.; Tetrahedron 42:3351–3403 (1986).

*Primary Examiner*—Douglas W. Robinson
*Assistant Examiner*—S. Saucier
*Attorney, Agent, or Firm*—Armstrong, Westerman, Hattori, McLeland & Naughton

[57] ABSTRACT

A method is proposed for manufacturing (−)-2-bromo-1-(3′-chlorophenyl) ethanol by bringing a 2-bromo-1-(3′-chlorophenyl) ethanone into contact with a microorganism belonging to 9 genuses including Ashbya genus and Brettanomycess genus to thereby reduce it asymmetrically into (−)-2-bromo-1-(3′-chlorophenyl) ethanol, and for manufacturing (−)-substituted styrene oxide by cyclizing the obtained alcohol under alkaline conditions. The (−)-substituted styrene oxide can be manufactured efficiently.

1 Claim, No Drawings

METHOD OF MANUFACTURING OPTICALLY ACTIVE (−)-2-HALO-1-(SUBSTITUTED PHENYL) ETHANOL BY KETONE REDUCTION

FIELD OF THE INVENTION

The present invention relates to a method of manufacturing (−)-2-halo-1-(substituted phenyl) ethanol and (−)-substituted styrene oxide and more particularly to a method of efficiently manufacturing (−)-2-halo-1-(substituted phenyl) ethanol by bringing a microorganism into contact with 2-halo-1-(substituted phenyl) ethanone and to a method of manufacturing (−)-substituted styrene oxide efficiently through cyclization thereof under alkaline conditions.

These compounds are useful as materials for synthesis of drugs, agrichemicals et cetera requiring to be optically active.

BACKGROUND OF THE INVENTION

As to optically active (−)-2-halo-1-(substituted phenyl) ethanol, the present inventors have not yet seen any patent, report or the like relating to its manufacture. Meanwhile, as to optically active chloro-substituted styrene oxide, there is a report that 72-86% e.e. could be achieved by epoxidation of chloro-substituted styrene by means of Nocardia corallina (Keizo Furuhasi; Organic Synthetic Chemistry, 43, 162 (1987)). Another known method of synthesis thereof is by interphase moving reaction between chloro-substituted benzaldehyde and dimethyl sulfonium methylide, but this method is extremely poor in optical purity attainable (Hiroyuki Sawada; Japanese Laid-open Patent Publication No. 105024/1976.

After having made intensive studies for development of an efficient method of manufacturing optically active (−)-2-halo-1-(substituted phenyl) ethanol and (−)-substituted styrene oxide, the present inventors discovered existence of some microorganisms capable of asymmetrically reducing 2-halo-1-(substituted phenyl) ethanone stereospecifically and converting it into (−)-2-halo-1-(substituted phenyl) ethanol and thus completed the invention.

DISCLOSURE OF THE INVENTION

The first aspect of the present invention is to provide a method of bringing a 2-halo-1-(substituted phenyl) ethanone represented by a general formula [1]

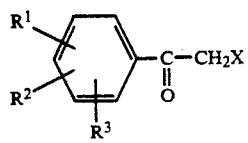

(1)

(where X represents a chlorine atom or a bromine atom and each of substitution groups $R^1$, $R^2$ and $R^3$ represents a hydrogen atom, a chlorine atom, a fluorine atom, a methyl group or a methoxy group except cases where 3 substitution groups are all hydrogen atoms) into contact with a microorganism selected from those belonging to Ashbya genus, Brettanomyces genus, Candida genus, Cryptococcus genus, Geortrichum genus, Pichia genus, Rhodosporidium genus, Rhodotorula genus, Saccharomyces genus, Torulopsis genus or Trigonopsis genus capable of reducing it asymmetrically into (−)-2-halo-1-(substituted phenyl) ethanol represented by a general formula [[2]

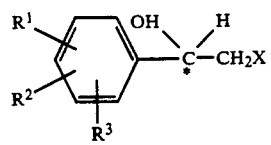

(2)

(where X and substitution groups $R^1$, $R^2$ and $R^3$ are the same as in the general formula [1] and * indicates an asymmetric carbon atom) and thereby to prepare (−)-2-halo-1-(substituted phenyl) ethanol.

The second aspect of the invention is to provide a method of manufacturing (−)-substituted styrene oxide represented by a general formula [3]

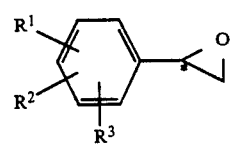

(3)

(where substitution groups $R^1$, $R^2$ and $R^3$ are the same as in the general formula [1] and [2] and * indicates an asymmetric carbon atom) by cyclizing under alkaline conditions (−)-2-halo-1-(substation phenyl) ethanol represented by the general formula [2]

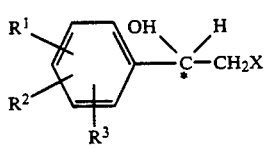

(2)

(where X and substitution groups $R^1$, $R^2$ and $R^3$ are the same as in the general formula [1] and * indicates an asymmetrical carbon atom).

OPTIMUM MODE OF EMBODYING THE INVENTION

The microorganism used in the present invention for asymmetrical reduction of 2-halo-1-(substituted phenyl) ethanone for conversion into (−)-2-halo-1-(substituted phenyl) ethanol can be found in the following way.

For example, 50 ml of A culture medium comprising 40 g of glucose, 3 g of yeast extract, 13 g of $(NH_4)_2HPO_4$, 7 g of $KH_2PO_4$, 0.8 g of $MgSO_4 \cdot 7H_2O$, 60 mg of $ZnSO_4 \cdot 7H_2O$, 90 mg of $FeSO_4 \cdot 7H_2O$, 5 mg of $CuSO_4 \cdot 5H_2O$, 10 mg of $MnSO_4 \cdot 4H_2O$ and 0.1 g of NaCl (per liter) is put into a 500 ml Sakaguchi flask, a given microorganism is inoculated after sterilization and the culture medium is cultured under shaking for 2 days at 30° C. Thereafter, cells are is collected by centrifugal separation, is suspended in 25 ml of 0.1M phosphate buffer solution (pH 7.0) containing 0.5% of 2-bromo-1-(3'-chlorophenyl) ethanone and 3% of glucose and shaken in a 500 ml Sakaguchi flask for 2-3 days at 30° C. It is then admixed with an equivalent amount of ethyl acetate, this followed by extraction, and the resulting (−)-2-bromo-1-(3'-chlorophenyl) ethanol is analyzed by gas chromatography (column: silicone OV-7, φ0.3×200 cm, column temperature 190° C., $N_2$ gas pressure 1.2 kg/cm²). The optical purity of (−)-2-bromo-1-(3'-chlorophenyl) ethanol can be determined by high-performance liquid chromatography (column: Nippon Bunko K. K.'s Chiralcel-OJ, dissolving solvent:hexane/isopropanol (50/1), flow rate: 1.0 ml/min., detection: 220 nm) after refining the extracted oil by distillation with the oil separated in 44.8 minutes of retention time for (−) isomer and 54.9 minutes of retention time for (+) isomer.

As microorganism may be used any of the known genuses capable of asymmetrical reduction of 2-halo-1-(substituted phenyl) ethanone for conversion into (−)-2-halo-1-(substituted phenyl) ethanol.

As such may be exemplified, among others, *Ashbya gossypii* IFO 0560, *Brettanomyces custersianus* IFO 1585, *Candida humicola* CBS 2774, *Candida intermedia* IFO 0761, *Candida krusei* IFO 0011, *Candida magnoliae* IFO 0705, *Candida pinus* IFO 0741, *Candida saitoana* IFO 0768, *Candida sake* CBS 2219, now available as IFO 1021 *Candida tropicalis* IFO 1403, *Cryptococcus albidus* IFO 0378, *Cryptococcus terreus* IFO 0727, Trichosporon CBS 7065, IFO 0574, *Pichia membranaefaciens* IFO 0460, *Rhodosporidium toruloides* IFO 0871, *Rhodotorula glutinis* IFO 1099, *Rhodotorula glutinis* var. dairenesis IFO 0415, *Rhodotorula graminis* IFO 0190, *Rhodotorula minuta* IFO 0387, *Rhodotorula rubra* IFO 0383, *Saccharomyces cerevisiae* IFO 0614 and *Trigonopsis variabilis* IFO 0671.

For the cultivation of these microorganisms may be used usually any nutriment which they can assimilate. For the cultivation thereof, therefore, may be used an ordinary culture media containing proper amounts of, for example, carbohydrates such as glucose and sucrose, alcohols such as ethanol and glycerol, hydrocarbons such as paraffin, organic acids such as acetic acid and propionic acids, carbon sources such as soy bean oil and mixtures thereof, yeast extracts, peptone, meat extracts, corn steep liquor, nitrogen-containing inorganic and organic nutriments such as ammonium sulfate and ammonia; inorganic nutriments such as phosphates, magnesium, iron, manganese and potassium, and vitamins such as biotin and thiamine. Cultivation is carried out aerobically for 1–5 days at 20°–40° C. with pH of the nutrient medium adjusted to 4.0–9.5.

As reducing method are known, for instance, a method in which a culture solution is used as it is and a method in which cells are separated by centrifugal separation and resuspended in, for example, a phosphate buffer solution or water and then it is admixed with 2-halo-1-(substituted phenyl) ethanone for reaction to proceed. For the reaction a carbon source such as glucose or sucrose may be added to the culture medium as an energy source. The cells may be used as live cells but may as well be used after acetone treatment or freeze drying. Such cells may also be used with them fixed on a carrier. 2-halo-1-(substituted phenyl) ethanone may be added as it is or after dissolution in an organic solvent lest it should interfere with the progress of the reaction either en bloc at the start of the reaction or in portions as the reaction proceeds. The reaction may be conducted under stirring for 3–120 hours at a temperature of 10°–60° C. with proper pH adjustment in a range of 5–9.

Separation of (−)-2-halo-1-(substituted phenyl) ethanol as the reaction product may be done directly from the reaction liquor or after separation of cells followed by extraction by the use of a solvent such as ethyl acetate and dichlormethane, dehydration and subsequent refining by distillation or silica gel chromatography, and in this way (−)-2-halo-1-(substituted phenyl) ethanol of a high purity can be obtained with ease. Its optical purity can be determined in the same way as described above by high-performance liquid chromatography by the use of column, Chiral cel-OJ and hexane/isopropanol (30–50/1) as eluate.

The (−)-2-halo-1-(substituted phenyl) ethanol thus obtained can be easily cyclized by heating or leaving at the room temperature under coexistence of an alkali such as NaOH in a quantity of not less than the equivalent mol and can be converted into (−)-substituted styrene oxide.

Hereinafter the present invention will be described in greater detail with reference to preferred examples but it is to be understood that the present invention is by no means limited thereby.

Unless otherwise noted, [%] in the following description means [weight %].

EXAMPLE 1

50 ml of the aforementioned A culture medium was put into a 500 ml Sakaguchi flask and after sterilization the microorganisms shown in Table 1 were inoculated thereon, and aerobical cultivation was carried out under shaking for 2 days at 30° C. Cells were taken from the culture solution by centrifugal separation, 0.5% of 2-bromo-1-(3'-chlorophenyl) ethanone was suspended in 25 ml of 0.1M phosphate buffer solution (pH 7.0) containing 0.3% glucose and reaction was carried out under shaking in the 500 ml Sakaguchi flask for 48 hours at 30° C. After completion of the reaction, (−)-2-bromo-1-(3'-chlorophenyl) ethanol was extracted twice using the equivalent amount of ethyl acetate and the resulting ethyl acetate layer was analyzed by gas chromatography for determination of the degree of conversion. Then, after dehydration of ethyl acetate with Glauber's salt anhydride, the solvent was removed and (−)-2-bromo-1-(3'-chlorophenyl) ethanol was obtained. This was dissolved in methylene chloride and its optical purity was determined by high-performance liquid chromatography. The results were as shown in Table 1.

TABLE 1

| | (−)-2-bromo-1-(3'-chlorophenyl) ethanol | |
|---|---|---|
| | Yield (%) | Optical purity (%) |
| *Ashbya gossypii* IFO 0560 | 55 | 72 |
| *Brettanomyces custersianus* IFO 1585 | 10 | 100 |
| *Candida humicola* CBS 2774 | 40 | 90 |
| *Candida intermedia* IFO 0761 | 54 | 100 |
| *Candida krusei* IFO 0011 | 31 | 100 |
| *Candida magnoliae* IFO 0705 | 80 | 81 |
| *Candida pinus* IFO 0741 | 44 | 92 |
| *Cryptococcus albidus* IFO 0378 | 59 | 92 |
| *Cryptococcus terreus* IFO 0727 | 63 | 98 |
| *Pichia farinosa* IFO 0574 | 44 | 81 |
| *Pichia membranaefaciens* IFO 0460 | 21 | 100 |
| *Rhodosporidium toruloides* IFO 0871 | 79 | 100 |
| *Rhodotorula glutinis* IFO 1099 | 56 | 67 |
| *Rhodotorula glutinis* var. dairenensis IFO 0415 | 75 | 100 |
| *Rhodotorula graminis* IFO 0190 | 51 | 100 |
| *Rhodotorula minuta* IFO 0387 | 8 | 99 |
| *Rhodotorula rubra* IFO 0383 | 56 | 100 |
| *Saccharomyces cerevisiae* IFO 0614 | 21 | 76 |
| *Trigonopsis variabilis* IFO 0671 | 76 | 88 |

EXAMPLE 2

*Rhodotorula glutinis* var. direnensis IFO 0415 was inoculated on 3 liters of A culture medium in a 5-liter minijar fermentator and cultivated for 24 hours under stirring (500 rpm.) at 30° C. with air being introduced at a rate of 1 vvm. After completion of cultivation, cells were collected by centrifugal separation and 7.5 g of 2-bromo-1-(3'-chlorophenyl) ethanone and 38 g of glucose were added and reaction was carried out for 24 hours at 30° C. under stirring (150 rpm.) with pH being adjusted to 7.0 by the use of NaOH. After the completion of the reaction, the reaction product was extracted twice using 750 ml of ethyl acetate. The ethyl acetate layer was first dehydrated using Glauber's salt anhydride, then the solvent was removed under reduced pressure and thus 5.2 g of an oily substance was obtained. This was distilled (130° C./3 mmHg) and there was obtained 3.9 g of colorless, oily (−)-2-bromo-1-(3'-chlorophenyl) ethanol. Its specific rotation $[\alpha]_D^{20}$ was −25.5° (c=1.02 $CH_3OH$) and its optical purity was 100% e.e. as it was determined by high-performance liquid chromatography.

H-NMR (90 MHz, $CDCl_3$) δ ppm 2.88 (br. S, 1H), 3.35–3.90 (m, 4H), 4.90 (d.d, J=315, 8 Hz, 1H) 6.98–7.51 (m, 4H)

EXAMPLE 3

Bio-reaction and analysis were carried out in the same way as described in Example 1 except that the microorganisms used were those shown in Table 2 and as substrate was used 2-bromo-1-(2'-chlorophenyl) ethanone instead of 2-bromo-1-(3'-chlorophenyl) ethanone and as the reaction product (−)-2-bromo-1-(2'-chlorophenyl) ethanol was obtained. The results were as shown in Table 2.

TABLE 2

| Microorganisms | (−)-2-bromo-1-(2'-chlorophenyl) ethanol | |
|---|---|---|
| | Yield (%) | Optical purity (%) |
| Candida humicola CBS 2774 | 23 | 92 |
| Candida intermedia IFO 0761 | 23 | 92 |
| Candida krusei IFO 0011 | 5 | 100 |
| Candida magnoliae IFO 0705 | 98 | 96 |
| Candida pinus IFO 0741 | 32 | 96 |
| Candida saitoana IFO 0768 | 13 | 91 |
| Candida sake IFO 1021 | 31 | 96 |
| Candida tropicalis IFO 1403 | 32 | 86 |
| Cryptococcus alibidus IFO 0378 | 15 | 98 |
| Cryptococcus terreus IFO 0727 | 39 | 100 |
| Trichosporon oubioeri CBS 7065 | 27 | 92 |
| Pichia farinosa IFO 0574 | 34 | 88 |
| Rhodosporidium toruloides IFO 0871 | 62 | 98 |
| Rhodotorula glutinis IFO 1099 | 87 | 100 |
| Rhodotorula glutinis ver. dairenensis IFO 0415 | 15 | 100 |
| Rhodotorula graminis IFO 0190 | 31 | 98 |
| Rhodotorula rubra IFO 0383 | 17 | 100 |
| Trigonopsis variabilis IFO 0671 | 7 | 99 |

EXAMPLE 4

Bio-reaction and analysis were conducted in the same way as described in Example 2 except that as microorganism was used Rhodotorula glutinis IFO 1099 and as substrate was used 2-bromo-1-(2'-chlorophenyl) ethanone and as the reaction product was obtained 4.2 g of (−)-2-bromo-1-(2'-chlorophenyl) ethanol.

Its specific rotation $[\alpha]_D^{20}$ was 41.5° (C=1.02, $CH_3OH$) and its optical purity as determined by high-performance liquid chromatography was 100% e.e.

H-NMR (90 MHz, $CDCl_3$) δ ppm 2.78–3.06 (m, 1H), 3.39 (d.d, J=9, 10 Hz, 1H), 3.73 (d.d, J=2.5, 10 Hz, 1H), 5.04–5.39 (m, 1H), 6.68–7.68 (m, 4H)

EXAMPLE 5

Bio-reaction and analysis were carried out in the same way as described in Example 2 except that as microorganisms were used those shown in Table 3 and as substrate was used 2-bromo-1-(4'-chlorophenyl) ethanone instead of 2-bromo-1-(3'-chlorophenyl) ethanone and as the reaction product (−)-2-bromo-1-(4'-chlorophenyl) ethanol was obtained. The results were as shown in Table 3.

TABLE 3

| Microorganisms | (−)-2-bromo-1-(4'-chlorophenyl) ethanol | |
|---|---|---|
| | Yield (%) | Optical purity (%) |
| Ashbya gossypii IFO 0560 | 47 | 95 |
| Burettanopmyces custersianus IFO 1585 | 11 | 100 |
| Candida humicola CBS 2774 | 51 | 73 |
| Candida intermedia IFO 0761 | 26 | 72 |
| Candida krusei IFO 0011 | 8 | 87 |
| Candida magnoliae IFO 0705 | 89 | 68 |
| Candida pinus IFO 0741 | 25 | 96 |
| Candida saitoana IFO 0768 | 55 | 98 |
| Candida tropicalis IFO 1403 | 21 | 90 |
| Cryptococcus alibidus IFO 0378 | 24 | 97 |
| Cryptococcus terreus IFO 0727 | 9 | 100 |
| Pichia falinosa IFO 0574 | 51 | 84 |
| Rhodosporidium toruloides IFO 0871 | 17 | 88 |
| Rhodotorula glutinis IFO 1099 | 55 | 93 |
| Rhodotorula glutinis var. direnensis IFO 0415 | 67 | 100 |
| Rhodotorula graminis IFO 0190 | 31 | 89 |
| Rhodotorula rubra IFO 0383 | 18 | 94 |
| Trigonopsis variabilis IFO 0671 | 42 | 76 |

EXAMPLE 6

Bio-reaction and analysis were carried out in the same way as described in Example 2 except that as substrate was used 2-bromo-1-(4'-chlorophenyl) ethanone instead of 2-bromo-1-(3'-chlorophenyl) ethanone and as the reaction product was obtained 3.6 g of (−)-2-bromo-1-(4'-chlorophenyl) ethanol.

Its boiling point was 115°–120° C./4 mmHg, specific rotation $[\alpha]_D^{20}$ was 26.6° (C=1.10, $CH_3OH$) and its optical purity as determined by high-performance chromatography was 100% e.e.

H-NMR (90 MHz, $CDCl_3$) δ ppm 2.77 (br, S, 1H), 3.18–3.70 (m, 2H), 4.82 (d.d, J=3.5, 7.5 Hz, 1H), 6.82–7.44 (m, 4H)

EXAMPLE 7

Bio-reaction and analysis were carried out in the same way as described in Example 2 except that as substrate was used 3.25 g each of 2-bromo-1-(2'-chlorophenyl) ethanone, 2-chloro-1-(3'-chlorophenyl) ethanone and 2-chloro-1-(4'-chlorophenyl) ethanone instead of 2-bromo-1-(3'-chlorophenyl) ethanone and as the reaction products (−)-2-chloro-1-(2'-chlorophenyl) ethanol, (−)-2-chloro-1-(3'-chlorophenyl) ethanol and (−)-2-chloro-1-(4'-chlorophenyl) ethanol were obtained respectively. The yields and physical properties of the respective reaction products were as shown in Table 4.

TABLE 4

| Substrate | 2-chloro-1- | 2-chloro-1- | 2-chloro-1- |
|---|---|---|---|

TABLE 4-continued

|  | (2'-chloro-phenyl)ethanone (−)-2-chloro-1-(2'-chlorophenyl)ethanol | (3'-chloro-phenyl)ethanone (−)-2-chloro-1-(3'-chlorophenyl)ethanol | (4'-chloro-phenyl)ethanone (−)-2-chloro-1-(4'-chlorophenyl)ethanol |
|---|---|---|---|
| Reaction product |  |  |  |
| Yield | 1.7 g | 1.4 g | 1.3 g |
| Boil. point | 150° C./5 mmHg | 130° C./3–4 mmHg | 140° C./5 mmHg |
| Specific rotation $[\alpha]_D^{20}$ (C = 1, CH$_3$OH) | −55.6° | −33.8° | −36.1° |
| Optical purity | 100% | 100% | 100% |
| H-NMR (90 MHz CDCl$_3$) δ ppm | 3.29(brs, S, 1H) 3.50(dd, J=11.5, 8.5Hz, 1H) 3.85(dd, J=11.5, 3Hz, 1H) 5.30(dd, J=11.5, 3Hz, 1H) 7.07–7.75(m, 4H) | 2.69(br, S, 1H) 3.27–3.90(m, 2H) 4.88(dd, J=3.5, 8Hz, 1H) 7.15–7.54(m, 4H) | 2.27(br, S, 1H) 3.41–3.82(m, 2H) 4.83(dd, J=4.5, 7.5Hz, 1H) 7.11–7.50(m, 4H) |

EXAMPLE 8

10 g each of (−)-2-halo-1-(chloro-substituted phenyl) ethanols obtained in Examples 2, 4, 6 and 7 was admixed with 5 ml of 40% NaOH aqueous solution and 10 ml of methylene chloride and was caused to react for 6 hours at 50° C. After cooling, the reaction product was admixed with 20 ml of methylene chloride, the methylene chloride layer was washed with saturated brine and after dehydration and filtration, methylene chloride was removed under reduced pressure and an oily epoxide was thus obtained. This was refined by distillation under reduced pressure and each (−)-chloro-substituted styrene oxide was obtained as shown in Table 5.

pressure and thus an oily substance was obtained. It was then distilled (105° C./4 mmHg) and 1.3 g of (−)-2-chloro-1-(4'-fluorophenyl) ethanol was obtained as a colorless oily substance. Its specific rotation $[\alpha]_D^{20}$ was 38.81° (c=1,01 CH$_3$OH) and its optical purity was 100% e.e. as it was determined by means of high-performance liquid chromatography.

1 g of this (−)-2-chloro-1-(4'-fluorophenyl) ethanol was then admixed with the equivalent mol of 40% aqueous solution of NaOH and 5 ml of methylene chloride and the mixture was caused to react for 6 hours at 50° C. After cooling, 5 ml of methylene chloride was added, the methylene chloride layer was washed with saturated brine and after dehydration and filtration, methylene chloride was removed under reduced pressure and

TABLE 5

|  | (−)-2-bromo-1-(3'-chloro phenyl)ethanol | (−)-2-chloro-1-(3'-chloro phenyl)ethanol | (−)-2-bromo-1-(2'-chloro phenyl)ethanol | (−)-2-bromo-1-(4'-chloro phenyl)ethanol |
|---|---|---|---|---|
| (−)-chloro-substituted styrene oxide | (−)-3'-chloro-styrene oxide |  | (−)-2'-chloro styrene oxide | (−)-4'-chloro styrene oxide |
| Yield | 6.2 g | 7.1 g | 5.4 g | 5.7 g |
| Boil. point | 90–93° C./5 mmHg | 90–93° C./5 mmHg | 80–85° C./4 mmHg | 85–90° C./4 mmHg |
| $[\alpha]_D^{20}$ (C = 1, CHCl$_3$) | −11.8° | −11.8° | −67.5° | −25.5° |
| H-NMR (90 MHz CDCl$_3$) δ ppm | 2.75(dd, J=2.5, 6Hz, 1H) 3.13(dd, J=3.5, 6Hz, 1H) 3.84(dd, J=2.5, 3.5Hz, 1H) 7.10–7.45(m, 4H) |  | 2.63(dd, J=2.5 6Hz, 1H) 3.15(dd, J=3, 6Hz, 1H) 4.17(dd, J=2.5 4Hz, 1H) 7.01–7.51(m, 4H) | 2.75(dd, 1H) 3.08(dd, 1H) 3.77(dd, 1H) 6.99–7.42(m, 14H) |

EXAMPLE 9

500 ml of the aforementioned A culture medium was put into a 2-liter Sakaguchi flask, Rhodotorula glutinis IFO 0415 was inoculated thereon, cultivation was done in the same way as described in Example 1, the resulting cells were collected, 1.5 g of 2-chloro-(4'-fluorophenyl) ethanone was suspended in 300 ml of 0.1M phosphate buffer solution (pH 7.0) containing 0.3% glucose, the suspension was put into the 2-liter Sakaguchi flask and it was reacted under shaking for 48 hours at 30° C. After the reaction was over, the reaction product was extracted twice using 300 ml of ethyl acetate. After dehydration of the ethyl acetate layer with Glauber's salt anhydride, the solvent was removed under reduced crude epoxide was obtained as an oily substance. This was refined under reduced pressure (85° C., 4 mmHg) and 0.65 g of (−)-4'-fluorostyrene oxide was obtained in a colorless oily form. Its specific rotation $[\alpha]_D^{20}$ was −20.96° (c=1.04 CHCl$_3$).

(−)-2-chloro-1-(4'-chlorophenyl) ethanol
H-NMR(90 MHz, CDCl$_3$) δ ppm 3.00 (S, 1H), 3.40–3.83 (m, 2H), 4.85 (d.d, J=4.5, 7.5 Hz, 1H) 6.83–7.53 (m, 4H)

(−)-4'-fluorostyrene oxide
H-NMR (90 MHz, CDCl3) δ ppm 2.72 (d.d, J=2.5, 6.0 Hz, 1H), 3.08 (d.d, J=4.5, 6.0 Hz, 1H), 3.82 (d.d. J=2.5, 4.0 Hz, 1H), 6.85–7.45 (m, 4H)

EXAMPLE 10

Cultivation, reaction and purification were carried out in the same way as described in Example 9 except that 2-chloro-1-(2', 4'-dichlorophenyl) ethanon, 2-chloro-1-(3', 4'-dichlorophenyl) ethanone, 2-chloro-1-(2', 5'-dichlorophenyl) ethanone were used as substrate, and (−)-2-chloro-1-(2', 4'-dichlorophenyl) ethanol, (−)-2-chloro-1-(3', 4'-dichlorophenyl) ethanol, (−)-2-chloro-1-(2', 5'-dichlorophenyl) ethanol was obtained. The yield, specific rotation and optical purity determined by high-performance liquid chromatography were shown in Table 6.

Then, epoxidated in the same way as Example 9, (−)-2', 4'-dichlorostyrene oxide, (−)-3', 4'-dichlorostyrene oxide, (−)-2', 5'-dichlorostyrene oxide were obtained. The yield and the specific rotation were as shown in Table 6.

and an oily substance was obtained. It was then refined by silica gel chromatography (hexane/ethyl acetate=7/1) and 1.1 g of a colorless oil of (−)-2-chloro-1-(2',3',4'-trichlorophenyl) ethanol was obtained. Its specific rotation $[\alpha]_D^{20}$ was −52.29° (C=1.07 $CH_3OH$) and its optical purity was 100% e.e. as it was determined by high-performance liquid chromatography.

(−)-2'-chloro-1-(2',3',4'-trichlorophenyl) ethanol
H-NMR(90 MHz, CDCl3) δ ppm 3.10(br,S,1H), 3.50(d,d, J=9.0, 11.0 Hz,1H) 3.85(d.d,J=3.0, 11.0 Hz,1H) 5.25(d.d,J=3.0, 8.5 Hz,1H) 7.35–7.59(m,2H)

EXAMPLE 12

Cultivation, reaction and purification were carried out in the same way as described in Example 9 except that 2-chloro-1-(2'-methylphenyl) ethanone, 2-chloro-1-(3'-methylphenyl) ethanone, 2-chloro-1-(4'-methylphenyl) ethanone were used as substrate, and (−)-2-chloro-

TABLE 6

| Substrate | 2-chloro-1-(2',4'-dichloro phenyl)ethanone | 2-chloro-1-(3',4'-dichloro phenyl)ethanone | 2-chloro-1-(2',5'-dichloro phenyl)ethanone |
|---|---|---|---|
| Reaction product | (−)-2-chloro-1-(2',4'-dichloro-phenyl)ethanol | (−)-2-chloro-1-(3',4'-dichloro-phenyl)ethanol | (−)-2-chloro-1-(2',5'-dichloro-phenyl)ethanol |
| Yield | 0.7 g | 0.8 g | 0.85 g |
| Form | Colorless oil | Colorless oil | Colorless oil |
| Boil. point | 160° C./4 mmHg | 170° C./4 mmHg | 140° C./4 mmHg |
| Specific rotation $[\alpha]_D^{20}$ (C = 1, $CH_3OH$) | −51.37° | −32.72° | −43.40° |
| Optical purity | 100% e.e. | 100% e.e. | 100% e.e. |
| H-NMR (90 MHz CDCl3) δ ppm | 2.86(br, S, 1H) 3.46–3.88(m, 2H) 4.96(dd, J=4.5, 7.0Hz, 1H) 7.13–7.70(m, 4H) | 2.95(br, S, 1H) 3.48(dd, J=8.5 11.5Hz, 1H) 3.85(dd, J=3.0, 11.4Hz, 1H) 5.18(dd, J=3.0, 8.5Hz, 1H) 7.18–7.65(m, 3H) | 2.98(br, S, 1H) 3.48(dd, J=9.0 12.0Hz, 1H) 3.85(dd, J=3.0, 11.0Hz, 1H) 5.25(dd, J=3,0, 8.5Hz, 1H) 7.35–7.59(m, 2H) |
| Reaction product | (−)-2',4'-dichloro styrene oxide | (−)-3',4'-dichloro styrene oxide | (−)-2',5'-dichloro styrene oxide |
| Yield | 0.61 g | 0.65 g | 0.68 g |
| Form | Colorless oil | Colorless oil | Colorless oil |
| Boil. point | 120° C./4 mmHg | 125° C./4 mmHg | 110° C./4 mmHg |
| Specific rotation $[\alpha]_D^{20}$ (C = 1, $CH_3OH$) | −61.30° | −18.30° | −22.15° |
| H-NMR (90 MHz CDCl3) δ ppm | 2.61(dd, J=2.5, 5.5Hz, 1H) 3.17(dd, J=3.0, 5.5Hz, 1H) 4.12(dd, J=2.5, 3.5Hz, 1H) 7.05–7.41(m, 3H) | 2.73(dd, J=2.5, 5.5Hz, 1H) 3.12(dd, J=4.0, 5.5Hz, 1H) 3.80(dd, J=2.5, 4.0Hz, 1H) 7.02–7.05(m, 3H) | 2.66(dd, J=3.0, 6.0Hz, 1H) 3.21(dd, J=5.5, 4.5Hz, 1H) 4.17(dd, J=3.0, 4.5Hz, 1H) 7.16–7.46(m, 3H) |

EXAMPLE 11

Cultivation and reaction were carried out in the same way as described in Example 9 except that 2-chloro-1-(2',3',4'-trichlorophenyl) ethane was used as substrate and, after the reaction was over, extraction was done twice using 300 ml ethyl acetate. The ethyl acetate layer was dehydrated with Glauber's salt anhydride, this followed by removal of solvent under reduced pressure, 1-(2'-methylphenyl) ethanol, (−)-2-chloro-1-(3'-methylphenyl) ethanol, (−)-2-chloro-1-(4'-methylphenyl) ethanol were obtained. The yield, specific rotation and optical purity determined by high-performance liquid chromatography were shown in Table 6.

Then, the reaction product was epoxidated in the same way as Example 9, and (−)-2'-methylstyrene oxide, (−)-3'-methylstyrene oxide, (−)-4'-methylstyrene oxide were obtained. The yield and the specific rotation were as shown in Table 7.

TABLE 7

| Substrate | 2-chloro-1-(2'-methyl phenyl)ethanone | 2-chloro-1-(3'-methyl phenyl)ethanone | 2-chloro-1-(4'-methyl phenyl)ethanone |
|---|---|---|---|
| Reaction product | (−)-2-chloro-1-(2'-methyl- | (−)-2-chloro-1-(3'-methyl- | (−)-2-chloro-1-(4'-methyl- |

TABLE 7-continued

| | phenyl)ethanol | phenyl)ethanol | phenyl)ethanol |
|---|---|---|---|
| Yield | 1.3 g | 1.2 g | 1.3 g |
| Form | Colorless oil | Colorless oil | Colorless oil |
| Boil. point | 110° C./4 mmHg | 115° C./4 mmHg | 120° C./4 mmHg |
| Specific rotation $[\alpha]_D^{20}$ (C = 1, CH$_3$OH) | −56.96° | −40.39° | −42.58° |
| Optical purity | 100% e.e. | 100% e.e. | 100% e.e. |
| H-NMR (90 MHz CDCl$_3$) δ ppm | 2.30(br, 3H)<br>2.72(br, S, 1H)<br>3.37–3.77(m, 2H)<br>5.03(dd, J=4.5, 8.5Hz, 1H)<br>7.01–7.61(m, 3H) | 2.35(S, 3H)<br>2.60(br, S, 1H)<br>3.46–3.85(m, 2H)<br>4.82(dd, J=5.0, 7.5Hz, 1H)<br>7.03–7.42(m, 4H) | 2.35(S, 3H)<br>2.68(br, S, 1H)<br>3.46–3.85(m, 2H)<br>4.85(dd, J=5.0, 7.5Hz, 1H)<br>7.00–7.40(m, 4H) |
| Reaction product | (−)-2′-methyl-styrene oxide | (−)-3′-methyl-styrene oxide | (−)-4′-methyl-styrene oxide |
| Yield | 0.8 g | 0.8 g | 0.8 g |
| Form | Colorless oil | Colorless oil | Colorless oil |
| Boil. point | 70° C./4 mmHg | 75° C./4 mmHg | 80° C./4 mmHg |
| Specific rotation $[\alpha]_D^{20}$ (C = 1, CH$_3$OH) | −80.59° | −23.01° | −29.46° |
| H-NMR CDCl$_3$ δ ppm | 2.39(br, 3H)<br>2.63(dd, J=2.5, 6.0Hz, 1H)<br>3.09(dd, J=3.0, 5.5Hz, 1H)<br>3.93(dd, J=2.5, 3.0Hz, 1H)<br>7.15(S, 4H) | 2.30(S, 3H)<br>2.69(dd, J=2.5, 6.0Hz, 1H)<br>3.03(dd, J=3.0, 6.0Hz, 1H)<br>3.74(dd, J=2.5, 3.0Hz, 1H)<br>6.89–7.29(m, 4H) | 2.30(S, 3H)<br>2.73(dd, J=2.5, 5.5Hz, 1H)<br>3.03(dd, J=4.5, 5.5Hz, 1H)<br>3.74(dd, J=2.5, 4.5Hz, 1H)<br>7.12(S, 4H) |

EXAMPLE 13

Cultivation, reaction and purification were carried out in the same way as described in Example 9 except that 2-chloro-1-(2′,4′-dimethylphenyl) ethanone and 2-chloro-1-(3′,4′-dimethylphenyl) ethanone were used as substrate, and (−)-2-chloro-1-(2′,4′-dimethylphenyl) ethanol and (−)-2-chloro-1-(3′,4′-dichlorophenyl) ethanol were obtained. The yield, specific rotation and optical purity determined by high-performance liquid chromatography were shown in Table 8.

Then, epoxidated in the same way as Example 9, (−)-2′,4′-dimethylstyrene oxide and (−)-3′,4′-dimethylstyrene oxide were obtained. The yield and the specific rotation were as shown in Table 8.

TABLE 8

| Substrate | 2-chloro-1-(2′,4′-dimethylphenyl)ethanone | 2-chloro-1-(3′,4′-dimethylphenyl)ethanone |
|---|---|---|
| Reaction product | (−)-2-chloro-1-(2′,4′-dimethylphenyl)ethanol | (−)-2-chloro-1-(3′,4′-dimethylphenyl)ethanol |
| Yield | 1.3 g | 1.3 g |
| Form | Colorless oil | Crystal (mp. 61.5° C.) |
| Boil. point | 130° C./4 mmHg | 125° C./4 mmHg |
| Specific rotation $[\alpha]_D^{20}$ (C = 1, CH$_3$OH) | −39.80° | −49.37° |
| Optical purity | 100% e.e. | 100% e.e. |
| H-NMR (90 MHz CDCl$_3$) δ ppm | 2.31(S, 6H)<br>2.59(br, S, 1H)<br>3.45–3.85(m, 2H)<br>5.08(dd, J=4.0, 9.0Hz, 1H)<br>6.90–7.56(m, 3H) | 2.28(S, 6H)<br>2.55(br, S, 1H)<br>3.60–3.80(m, 2H)<br>4.85(dd, J=4.5, 7.5Hz, 1H)<br>7.00–7.31(m, 3H) |
| Reaction product | (−)-2′,4′-dimethyl-styrene oxide | (−)-3′,4′-dimethyl-styrene oxide |
| Yield | 0.76 g | 0.73 g |
| Form | Colorless oil | Colorless oil |
| Boil. point | 90° C./4 mmHg | 88° C./4 mmHg |
| Specific rotation $[\alpha]_D^{20}$ (C = 1, CH$_3$OH) | −69.14° | −29.03° |
| H-NMR (90 MHz CDCl$_3$) δ ppm | 2.28(S, 3H)<br>2.35(S, 3H)<br>2.65(dd, J=3.0, 6.0Hz, 1H)<br>3.08(dd, J=3.0, 6.0Hz, 1H)<br>3.98(dd, J=3.0, 4.0Hz, 1H)<br>6.83–7.26(m, 3H) | 2.22(S, 6H)<br>2.73(dd, J=2.5, 5.5Hz, 1H)<br>3.05(dd, J=4.0, 5.5Hz, 1H)<br>3.75(dd, J=2.5, 4.0Hz, 1H)<br>6.88–7.27(m, 3H) |

EXAMPLE 14

Cultivation, reaction and purification were carried out in the same way as described in Example 9 except that 2-chloro-1-(2'-methoxyphenyl) ethanone, 2-chloro-1-(3'-methoxyphenyl) ethanone, 2-chloro-1-(4'-methoxyphenyl) ethanone were used as substrate and (−)-2-chloro-1-(2'-methoxyphenyl) ethanol, (−)-2-chloro-1-(3'-methoxyphenyl) ethanol and (−)-2-chloro-1-(4'-methoxyphenyl) ethanol were obtained. The yield, specific rotation and optical purity determined by high-performance liquid chromatography were shown in Table 9.

Then, by epoxidation in the same way as Example 9 (−)-2'-methoxystyrene oxide, (−)-3'-methoxystyrene oxide and (−)-4'-methoxystyrene oxide were obtained. The yield and the specific rotation were as shown in Table 9.

TABLE 9

| Substrate | 2-chloro-1-(2'-methoxyphenyl)ethanone | 2-chloro-1-(3'-methoxyphenyl)ethanone | 2-chloro-1-(4'-methoxyphenyl)ethanone |
|---|---|---|---|
| Reaction product | (−)-2-chloro-1-(2'-methoxyphenyl)ethanol | (−)-2-chloro-1-(3'-methoxyphenyl)ethanol | (−)-2-chloro-1-(4'-methoxyphenyl)ethanol |
| Yield | 1.4 g | 1.4 g | 1.4 g |
| Form | Colorless oil | Colorless oil | Colorless oil |
| Boil. point | 135° C./4 mmHg | 140° C./4 mmHg | 145° C./4 mmHg |
| Specific rotation $[\alpha]_D^{20}$ (C = 1, $CH_3OH$) | −68.25° | −34.74° | −41.50° |
| Op. purity | 100% e.e. | 100% e.e. | — |
| H-NMR (90 MHz $CDCl_3$) δ ppm | 3.00(br, S, 1H) 3.40–4.00(m, 2H) 3.83(S, 3H) 5.12(dd, J=5.5, 8.5Hz, 1H) 6.74–7.56(m, 4H) | 2.80(br, S, 1H) 3.78(S, 3H) 3.43–3.90(m, 2H) 4.83(dd, J=4.5, 7.5Hz, 1H) 6.73–7.47(m, 4H) | 2.82(br, S, 1H) 3.36–3.90(m, 2H) 3.78(S, 3H) 4.85(dd, J=5.5, 7.5Hz, 1H) 6.93(d, J=9.0 Hz, 2H) 7.33(d, J=9.0, Hz, 2H) |
| Reaction product | (−)-2'-methoxystyrene oxide | (−)-3'-methoxystyrene oxide | (−)-4'-methoxystyrene oxide |
| Yield | 0.7 g | 0.7 g | 0.7 g |
| Form | Colorless oil | Colorless oil | Colorless oil |
| Boil. point | 110° C./4 mmHg | 115° C./4 mmHg | 120° C./4 mmHg |
| Specific rotation $[\alpha]_D^{20}$ (C = 1, $CH_3OH$) | −58.95° | −14.95° | −23.00° |
| H-NMR (90 MHz $CDCl_3$) δ ppm | 2.68(dd, J=2.5, 6.0Hz, 1H) 3.12(dd, J=3.0, 6.0Hz, 1H) 3.85(S, 3H) 4.20(dd, J=2.5, 3.0Hz, 1H) 6.76–7.43(m, 4H) | 2.73(dd, J=2.5, 6.0Hz, 1H) 3.05(dd, J=5.5, 6.0Hz, 1H) 3.75(S, 3H) 3.56–3.92(m, 1H) 6.61–7.40(m, 4H) | 2.75(dd, J=2.5, 5.5Hz, 1H) 3.04(dd, J=4.5, 5.5Hz, 1H) 3.75(S, 3H) 3.47–3.87(m, 1H) 6.83(d, J=9.0, Hz, 2H) 7.16(d, J=9.0, Hz, 2H) |

EXAMPLE 15

Cultivation, reaction and purification were carried out in the same way as described in Example 9 except that 2-chloro-1-(2',5'-dimethoxyphenyl) ethanone, 2-chloro-1-(3',4'-dimethoxyphenyl) ethanone were used as substrate and (−)-2-chloro-1-(2',5'-dimethoxyphenyl) ethanol, (−)-2-chloro-1-(3',4'-dimethoxyphenyl) ethanol were obtained. The yield, specific rotation and optical purity determined by high-performance liquid chromatography were shown in Table 10.

Then, by epoxidation of (−)-2-chloro-1-(2',5'-dimethoxyphenyl) ethanol in the same way as Example 9 (−)-2',5'-dimethoxystyrene oxide was obtained. The yield and the specific rotation were as shown in Table 10.

TABLE 10

| Substrate | 2-chloro-1-(2',5'-dimethylphenyl)ethanone | 2-chloro-1-(3',4'-dimethylphenyl)ethanone |
|---|---|---|
| Reaction product | (−)-2-chloro-1-(2',5'-dimethoxypheny)ethanol | (−)-2-chloro-1-(3',4'-dimethoxypheny)ethanol |
| Yield | 1.4 g | 1.3 g |
| Form | Colorless oil | Colorless oil |
| Boil. point | 150° C./4 mmHg | 175° C./4 mmHg |
| Specific rotation $[\alpha]_D^{20}$ (C = 1, $CH_3OH$) | −51.27° | −25.59° |
| Optical purity | 100% e.e. | 100% e.e. |
| H-NMR | 3.16(br, S, 1H) | 2.80(br, S, 1H) |

TABLE 10-continued

| (90 MHz CDCl₃) δ ppm | 3.73(S, 3H)<br>3.77(S, 3H)<br>3.40-3.93(m, 2H)<br>5.08(dd, J=4.0, 8.0Hz, 1H)<br>6.60-7.10(m, 3H) | 3.85(S, 6H)<br>3.40-3.80(m, 2H)<br>4.75(dd, J=6.0, 7.5Hz, 1H)<br>6.60-7.05(m, 3H) |
|---|---|---|
| Reaction product | (−)-2'-5'-dimethoxy-styrene oxide | |
| Yield | 0.7 g | |
| Form | Colorless oil | |
| Boil. point | 140° C./4 mmHg | |
| Specific rotation [α]$_D^{20}$ (C = 1, CH₃OH) | −33.47° | |
| H-NMR (90 MHz CDCl₃) δ ppm | 2.64(dd, J=2.5, 6.0Hz, 1H)<br>3.08(dd, J=4.0, 6.0Hz, 1H)<br>3.72(S, 3H)<br>3.79(S, 3H)<br>4.15(dd, J=2.5, 4.0Hz, 1H)<br>6.55-7.05(m, 3H) | |

EXAMPLE 16

Cultivation and reaction were carried out in the same way as described in Example 9 except that 2-chloro-1-(2',3',4'-trimethoxyphenyl) ethanone, 2-chloro-1-(3',4',5'-trimethoxyphenyl) ethanone were used as substrate and after completion of reaction, extraction was done twice using 300 ml of ethyl acetate. After dehydration of the ethyl acetate layer, the solvent was removed under reduced pressure, the resulting oily substance was refined by silica gel chromatography (hexane/ethyl acetate=7/1) and (−)-2-chloro-1-(2',3',4'-trimethoxyphenyl) ethanol, (−)-2-chloro-1-(3',4',5'-trimethoxyphenyl) ethanol were obtained. Their yield and specific rotation were as shown in Table 11.

TABLE 11

| Substrate | 2-chloro-1-(2',3',4'-trimethoxyphenyl)ethanone | 2-chloro-1-(3',4',5'-trimethoxyphenyl)ethanone |
|---|---|---|
| Reaction product | (−)-2-chloro-1-(2',3',4'-trimethoxyphenyl)ethanol | (−)-2-chloro-1-(3',4',5'-trimethoxyphenyl)ethanol |
| Yield | 1.2 g | 1.3 g |
| Form | Colorless oil | Crystal (mp. 65.5° C.) |
| Specific rotation [α]$_D^{20}$ (C = 1, CH₃OH) | −22.05° | −24.76° |
| Optical purity | — | — |
| H-NMR (90 MHz CDCl₃) δ ppm | 2.89(br, S, 1H)<br>3.86(S, 6H)<br>3.96(S, 3H)<br>3.42-4.23(m, 2H)<br>5.08(dd, J=3.5, 7.5Hz, 1H)<br>6.71(d, j=9.0, Hz, 1H)<br>7.16(d, J=9.0, Hz, 1H) | 2.82(br, S, 1H)<br>3.36-3.76(m, 2H)<br>3.80 (S, 3H)<br>3.84(S, 6H)<br>4.80(dd, J=4.5, 7.5Hz, 1H)<br>6.60(S, 1H) |

INDUSTRIAL APPLICATION POSSIBILITY

As shown in the examples, the present invention enables efficient manufacture of optically active (−)-2-halo-1-(substituted phenyl) ethanol and (−)-substituted styrene oxide.

We claim:

1. A method of preparing a (−)-2-halo-1-(substituted phenyl) ethanol of the formula

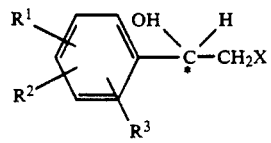

wherein X is chlorine or bromine and each of R¹, R², R³ is hydrogen, chlorine, fluorine, methyl or methoxy, and wherein R¹, R² and R³ are not all hydrogen at the same time, and * indicates an asymmetric carbon atom, which comprises subjecting a 2-halo-1-(substituted phenyl) ethanone of the formula

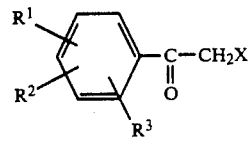

to the action of a microorganism selected from the group consisting of *Ashbya gossypii* IFO 0560, *Brettanomyces custersianus* IFO 1585, *Candida intermedia* IFO 0761, *Candida krusei* IFO 0011, *Candida magnoliae* IFO 0705, *Candida pinus* IFO 0741, *Candida saitoana* IFO 0768, *Candida tropicalis* IFO 1403, *Cryptococcus albidus* IFO 0378, *Cryptococcus terreus* IFO 0727, *Trichosporon loubieri* CBS 7065, *Pichia farinosa* IFO 0574, *Pichia membranaefaciens* IFO 0460, *Rhodosporidium toruloides* IFO 0871, *Rhodotorula graminis* IFO 0190, *Rhodotorula minuta* IFO 0387, *Rhodotorula rubra* IFO 0383, *Saccharomyces cerevisiae* IFO 0614 and *Trigonopsis variabilis* IFO 0671 and recovering said substituted phenyl ethanol. P

* * * * *